United States Patent [19]

Chance

[11] 4,023,905
[45] May 17, 1977

[54] FLASH PHOTOLYSIS SPLIT BEAM SPECTROPHOTOMETER

[76] Inventor: Britton Chance, c/o Johnson Research Foundation, School of Medicine, University of Pennsylvania, Philadelphia, Pa. 19174

[22] Filed: Dec. 29, 1975

[21] Appl. No.: 644,863

[52] U.S. Cl. .............................. 356/97; 23/230 B; 23/253 R; 356/85; 356/95
[51] Int. Cl.$^2$ ......................................... G01J 3/42
[58] Field of Search ................. 23/230 B, 253 R; 356/85, 88, 93–97; 250/573–576

[56] References Cited

UNITED STATES PATENTS

| 3,811,777 | 5/1974 | Chance | 356/85 |
| 3,830,222 | 8/1974 | Chance | 356/39 |

OTHER PUBLICATIONS

Boxall et al., Proc. R. Soc. Lond.; vol. 328, No. 1575, 1972, pp. 515–527.

*Primary Examiner*—John K. Corbin
*Assistant Examiner*—F. L. Evans
*Attorney, Agent, or Firm*—Herman L. Gordon

[57] ABSTRACT

Method and apparatus for providing flash photolysis of CO-inhibited cytochrome oxidase in a first portion of a sample exposed to an oxygenating agent and optically comparing the result with a non-photolyzed second portion of the sample or with a previously photolyzed portion of the sample. The sample is contained in a tubular transparent chamber located in the optical scanning path of a split-beam spectrophotometer having respective split-beam light guide channels traversing two spaced portions of the tubular sample chamber. Two corresponding photolyzing light guide channel assemblies are provided perpendicular to the scanning light guide channels, coplanar therewith, with a laser adjustably positioned to selectively flash-illuminate either of the two transverse photolyzing light guide channels optically communicating with the sample chamber. The technique may be employed either with frozen samples or with samples in the liquid state, with the viscosity suitably increased and with a constriction between the two portions of the sample chamber to inhibit mixing.

17 Claims, 5 Drawing Figures

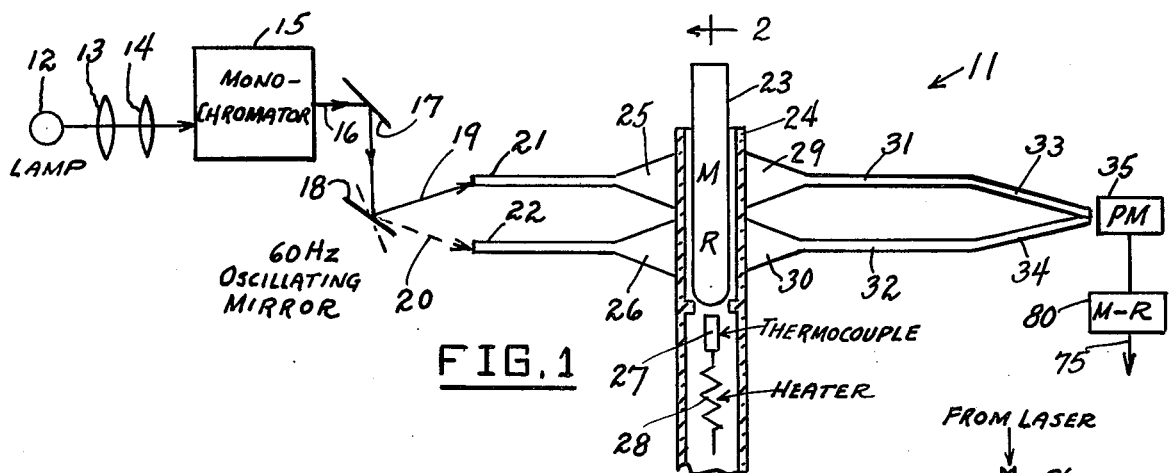
FIG.1
FIG.3
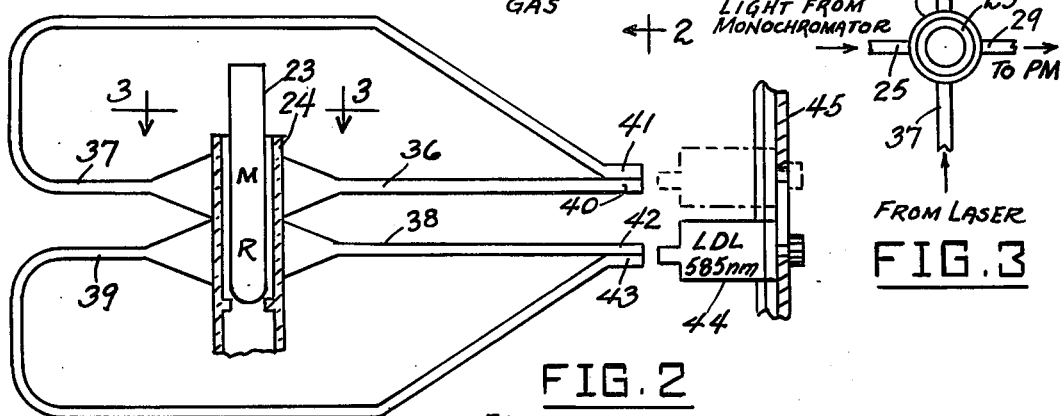
FIG.2
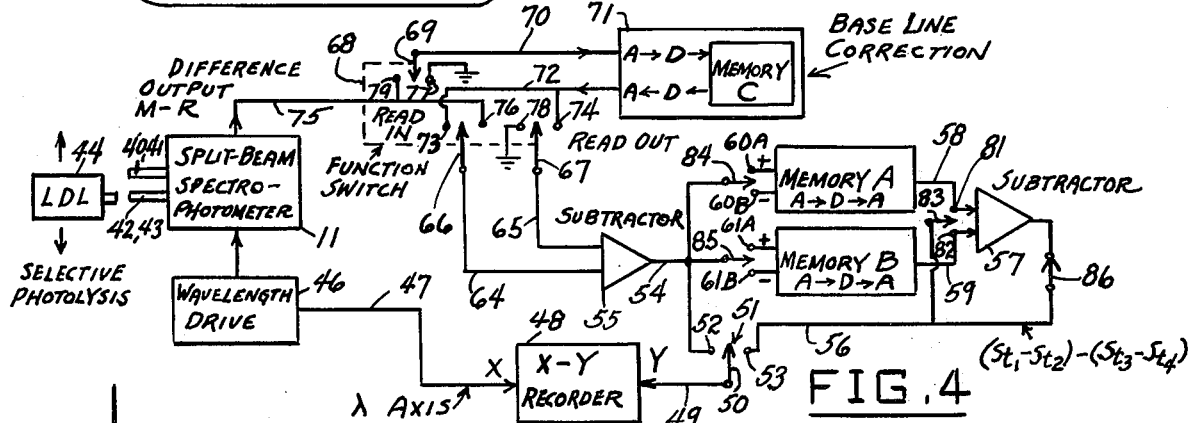
FIG.4
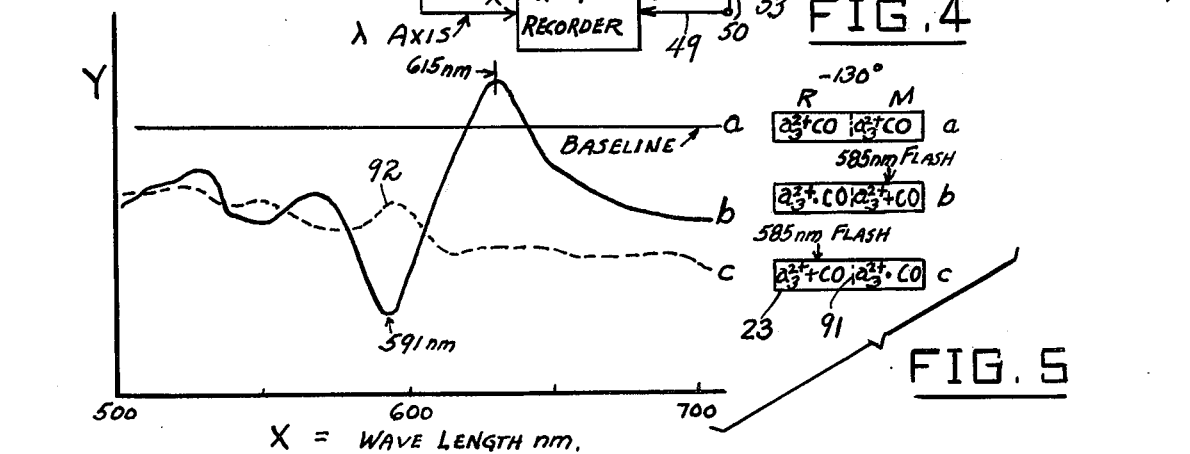
FIG.5

FLASH PHOTOLYSIS SPLIT BEAM SPECTROPHOTOMETER

This invention relates to spectrophotometry, and more particularly to a spectrophotometric method and apparatus for analyzing an oxidation-inhibited sample exposed to an oxidizing agent, which is flash-photolyzed.

A main object of the invention is to provide a novel and improved technique for providing flash photolysis of an oxidationinhibited sample exposed to an oxidizing agent and for optically analyzing the result.

A further object of the invention is to provide an improved method and apparatus for providing flash photolysis of an oxidation-inhibited sample exposed to an oxidizing agent and optically comparing the result with a non-photolyzed second portion of the sample or with a previously photolyzed portion of the sample, the method involving relatively simple steps and the apparatus being easy to operate and providing a reliable and accurate comparison over a spectrum of interest.

A still further object of the invention is to provide an improved method and apparatus for providing flash photolysis of COinhibited cytochrome oxidase in a first portion of a sample exposed to an oxidizing agent and optically comparing the result with a non-photolyzed second portion of the sample or with a previously photolyzed portion of the sample, the method employing a split-beam spectrophotometric technique wherein time-shared beams traverse two spaced portions of a sample chamber containing the CO-inhibited cytochrome oxidase and the oxidizig agent, one portion being flash-photolyzed, and the apparatus providing a readout in the form of a spectral curve showing the difference of the spectral absorbances of the two scanned portions of the sample chamber, whereby the interactions of energy coupling of cytochrome oxidase with various oxidizing agents can be conveniently studied and wherein the spectral curve provides important information regarding the sample under study, which can be employed for diagnostic and other purposes.

A still further object of the invention is to provide an improved method and apparatus for studying reactions of cytochrome oxidase with oxygen, wherein the cytochrome oxidase is CO-inhibited and maintained at a relatively low temperature to facilitate effective study of the kinetics of the oxygen reaction in suspensions of intact mitochondria without loss of electron transport or energy coupling activities, wherein flash photolysis activation of the cytochrome oxidase-oxygen reaction is employed, along with spectroscopic recording of the changes caused by the reaction, and wherein a dual-beam scanning technique is employed for obtaining difference spectra between the CO-inhibited oxidase and the $O_2$-combined oxidase and of the forms of the oxygen compounds generated following the flash photolysis.

A still further object of the invention is to provide an improved method and apparatus for recording the spectra of energy-dependent interconversion of compounds formed by the flash photolysis of CO-inhibited cytochrome oxidase at low temperature in the presence of an oxidizing agent, by wavelength scanning to compare absorbancy differences between two different parts of the same sample chamber, one of which has been flash-photolyzed while the other contains the CO-inhibited material, thereby taking advantage of observing the reaction kinetics in the solid phase in which mixing cannot take place at a significant rate.

A still further object of the invention is to provide a method and apparatus for recording the spectra of the reactants in all types of photochemical reactions that can be light-activated, including all those of photochemistry, particularly those of photosynthesis, and more particularly if intermediates can be observed in the liquid state of the preparation under study in two adjacent parts of a tubular container in times shorter than those required for mixing of the contents of said two parts; longer-lived intermediates can be observed by maintaining the material in a frozen state, where mixing of the contents of the two parts of the tubular container does not occur.

Further objects and advantages of the invention will become apparent from the following description and claims, and from the accompanying drawings, wherein:

FIG. 1 is a vertical cross-sectional view, partly in block diagram form, of a split-beam photolysis spectrophotometer constructed in accordance with an employing the method of the present invention.

FIG. 2 is a vertical cross-sectional view taken substantially on the line 2—2 of FIG. 1.

FIG. 3 is a fragmentary top plan view of the cuvette portion of the spectrophotometer, taken substantially on line 3—3 of FIG. 2.

FIG. 4 is a block diagram showing the electronic components of the split-beam spectrophotometer of FIGS. 1 to 3.

FIG. 5 illustrates the recordings obtained of difference spectra of a typical cytochrome sample treated in accordance with the method of the present invention and derived from the apparatus of FIGS. 1 to 4.

Various techniques and apparatus have been previously employed for the study of the reaction of cytochrome oxidase with oxygen. These techniques have included the use of flash photolysis for triggering the oxidation reaction. Examples of such techniques are disclosed in U.S. Pat. Nos. 3,830,222 and 3,811,777 to Britton Chance. In procedures of this type the cytochrome oxidase is blocked with carbon monoxide, and no reaction occurs until flash photolysis, for example, with a liquid dye laser at 585 nm.

As a typical example, the regenerative flow apparatus, used with a flash photolysis attachment, at room and low temperatures has afforded an affective approach to the study of the effects of ATP on the reaction of cytochrome oxidase with oxygen. In such a study, the mitochondrial suspension was allowed to become anaerobic and equilibrated with carbon monoxide, and then driven through the observation chamber of the flow apparatus, being mixed with oxygen therein. Because cytochrome oxidase was blocked with CO, no reaction occurred until flash photolysis with a liquid dye laser at 585 nm. The experiments were made with and without pre-treatment with ATP or the injection of oxygen at the time of the flow. Using suitable monochromatic observation beams, absorbance vs. time curves were obtained showing the effects of the flash photolysis under the different conditions. The comparison of the initial rates of the reaction 100 microseconds after the flash, with and without ATP, with samples in which oxygen had been mixed provided significant information as to the effect of the ATP.

Various other experiments may be devised to study the kinetics of cytochrome oxidation. However, it has been found that at room temperature the steady state concentrations of the intermediate involved in energy coupling are too low for their effects on the reaction kinetics to be observed, and that partial reactions of cytochrome oxidase with oxygen must be studied in order to identify energy coupling events. The pursuit of intermediates in the reaction of cytochrome oxidase with oxygen has led to the study of the reaction at lower temperatures and to the use of non-aqueous solvents; thus the kinetics of the oxygen reaction can be studied effectively in suspensions of intact mitochondria, without loss of electron transport or energy coupling activities.

A suitable low temperature approach consists of oxygenation of CO-inhibited suspensions of mitochondria at approximately −30° C, cooling to −80° C with subsequent equlibration at the temperature at which the kinetic recordings are desired, flash photolysis of the cytochrome oxidase-oxygen reaction, and spectroscopic recording of the changes caused by this reaction. In accordance with the present invention, a split-beam scanning technique is employed for obtaining difference spectra between the CO-combined oxidase and the $O_2$-combined oxidase, and of the forms of the oxygen compounds which follow. The technique involves the use of a wavelength-scanning spectrophotometer which compares absorbancy differences between different parts of the same sample tube, one of which has been flash-photolyzed and reacted with oxygen while the other remains in the form of the CO compound, thereby taking advantage of observing the reaction kinetics in the solid phase in which mixing cannot take place at a significant rate. Also, since different sample tubes, and different parts of the same sample tube have different optical properties, caused by variations in the thickness of the tubes, and because of variations in transmission of light guides employed and other residual differential errors of the system, the apparatus includes means to store and make the appropriate base line corrections to compensate for these factors.

While the technique contemplated by the present invention can be carried out most conveniently with the sample in a frozen state, it is also feasible to employ the technique with the sample in the liquid state with the viscosity increased by added "anti-freeze" and when a constriction is present in the sample tube to inhibit mixing.

Referring to the drawings, 11 generally designates a split-beam flash photolysis spectrophotometer for recording the spectra of the energy-dependent interconversion of the compounds, employing the above-described technique. The apparatus 11 comprises a suitable light source 12 whose radiation is directed through lenses 13, 14 to a wavelength scanning monochromator 15, which furnishes a wavelength scanning beam 16. Beam 16 is reflected by a fixed plane mirror 17 to an oscillating mirror 18 and is thereby split into two time-shared beam 19 and 20 which are respectively imaged upon the two spaced light guides 21 and 22.

A sample tube 23, which may be similar to that employed with low temperature equipment designed for EPR (electron paramagnetic resonance) studies, is suitably supported in the upper neck portion 24 of a Dewar flask containing liquid nitrogen. The light guides 21, 22 have respective flared output end portions 25 and 26 optically exposed to the upper and lower portions of the sample tube 23, which is tranparent.

The temperature of the sample is regulated by a thermocouple 27 and feedback control heater 28 which adjusts the temperature of the cold nitrogen in neck 24 to the desired value.

Light transmitted from the output members 25 and 26 through the Dewar neck portion 24 and the sample tube 23 enters respective flared light guide input members 29 and 30 aligned with output members 25 and 26 and leading to light guides 31 and 32 whose ends are brought together at 33 and 34 to impinge on a single photomultiplier detector tube 35, giving time-shared signals as an output, corresponding to the M (upper) and R (lower) parts of the sample tube. The time-shared M and R output signals from the photomultiplier tube are processed to obtain their difference by conventional circuitry 80, the difference spectral signal appearing in the output line 75. As shown in FIG. 1, the aligned guide end elements 25, 29 and 26, 30 are located in a common vertical diametral plane of tube 23.

Photolysis is provided by four sets of light guides 36, 37, 38 and 39 located in a diametral plane orthogonal to the direction of the M and R light paths, namely, perpendicular to the plane of light guides 21, 31, 22, 32. The upper light guides 36, 37 are brought together at flash receptor end portions 40, 41 and the lower light guides 38, 39 are brought together at flash receptor end portions 42, 43, the receptor portions 40, 41 and 42, 43 being in vertical alignment, as shown in FIG. 2, and located to be selectively flash-illuminated by a liquid dye laser unit 44 adjustably supported on a vertical guide track 45. In its lowermost position, laser unit 44 is optically aligned with receptor portions 42, 43, and in its uppermost position, shown in dotted view in FIG. 2, said laser unit is optically aligned with receptor portions 40, 41.

Upper flash guides 36, 37 are substantially in the same horizontal plane as measure beam light guides 21, 31, and lower flash guides 38, 39 are substantially in the same horizontal plane as reference beam guides 22, 32. The upper flash guides 36, 37 are located to simultaneously flash-illuminate diametrically opposite sides of the upper space in tube 23 and the lower guides 38, 39 are located to simultaneously flash-illuminate diametrically opposite sides of the lower space in tube 23.

It will be seen that with the above-described arrangement, a frozen sample in tube 23 can be established in two different chemical states in the same sample tube. As above mentioned, the two states can be established most conveniently with the sample in a frozen condition. However, this is also feasible with the sample in a liquid state when the viscosity of the sample is suitably increased by the addition of antifreeze and by providing a constriction in the tube between its upper and lower portions to inhibit mixing.

FIG. 4 schematically shows the electronic components of a typical split-beam photolysis spectrohotometer read-out system employed with the spectrophotometer assembly of FIGS. 1 to 3. A conventional wavelength drive device 46 is connected to the scanning monochromator of the spectrophotometer 11 and provides a wavelength axis signal via line 47 to the X input terminal of an X–Y recorder 48. The Y input to the recorder is provided via a line 49 and the pole 50 of a two-contact selector switch 51 having the contacts 52 and 53. Contact 52 is connected to the output line 54 of a subtractor 55. Contact 53 is connected to the output line 56 of a subtractor 57. Line 56 is connected to the output of the subtractor 57 through a control switch 86. The inputs of subtractor 57 are connected to respective switch contacts 81, 82 connected by lines 58, 59 to the outputs of respective conventional analog-digital input, digital-analog output memory devices A and B. Contacts 81, 82 are selectively engageable by a switch pole 83 connected to line 56, for thereby connecting the output of either memory device A or B to line 56 if so desired.

The memory devices A and B have respective additive inputs connected to switch contacts 60A and 61A, and have respective subtractive inputs connected to switch contacts 60B and 61B. Switch contacts 60A and 60B are selectively engageable by a switch pole 84, and switch contacts 61A and 61B are selectively engageable by a switch pole 85. The switch poles 84 and 85 are connected to the output line 54 of subtractor 55.

The input lines 64, 65 of subtractor 55 are respectively connected to two of the poles 66 and 67 of a two-position, three-section function switch 68. The remaining pole 69 of this switch is connected via a line 70 to the input of a baseline correction memory device 71. The output line 72 of memory device 71 is connected to a switch contact 73 engageable by a pole 66 in its leftward switch-closing position, as viewed in FIG. 4, and to a switch contact 74 engagable by switch pole 67 in its rightward closing position.

The M minus R output of the spectrophotometer 11 is connected by the line 75 to the switch contact 76, engageable by pole 66 in its rightward closing position.

The rightward-closing contact 77 associated with pole 69 and the leftward-closing contact 78 assosicated with pole 67 are grounded.

Spectral baseline correction data, comprising differential absorbance of the upper and lower portions of the empty sample tube 23 and associated light channels may be read into and stored in the memory device 71 by leftward operation of the function switch pole 69 to cause it to engage a contact 79 connected to line 75, to thereby store the spectral corrections required due to the above-mentioned optical differences. This stored data can be subsequently applied to any subsequent spectrum read out from spectrophotometer 11 by rightward closure of switch pole 67 with contact 74, to deliver the correction spectrum to one input of subtractor 55 via line 65, while pole 66 engages contact 76 to apply the M minus R difference output to the other input of subtractor 55 via line 64. The corrected split-beam spectral data can then be furnished (1) additively or subtractively (via pole 84 and contacts 60A, 60B or pole 85 and contacts 61A, 61B) to memory device A or memory device B, or (2) directly to the Y input line 49 by leftward closure of pole 50 of selector switch 51.

Spectral data stored respectively in memory A and memory B may be subtracted by subtractor 57 to provide A minus B spectral data and may be furnished to the recorder Y input line 49 by rightward closure of pole 50 of selector switch 51.

As above mentioned, the memory devices A and B and the memory device 71 may be conventional analog-digital input, digital-analog output storage devices well known in the art. The devices A and B have additive inputs at contacts 60A and 61A, and have subtractive inputs at 60B and 61B. Thus, a difference spectrum $S_{t1}$, taken at a time $t_1$ may be stored in memory A via contact 60A, and a difference spectrum $S_{t2}$, taken at a subsequent time $t_2$ may be subtracted from $S_{t1}$ via contact 60B, giving a resultant stored difference spectrum $(S_{t1} - S_{t2})$ in memory A. Similarly, a difference spectrum $S_{t3}$, taken at a subsequent time $t_3$ may be stored in memory B via contact 61A, and a difference spectrum $S_{t4}$, taken at a further subesequent time $t_4$, may be subtracted from $S_{t3}$ via contact 61B, giving a resultant stored difference spectrum $(S_{t3} - S_{t4})$ in memory B. The available difference spectrum output of subtractor 57 will then be $(S_{t1} - S_{t2})$ minus $(S_{t3} - S_{t4})$.

In a typical mode of operation, the optical correction spectrum is first stored in memory device 71 in the manner above described, with tube 23 empty. Then, with the sample in tube 23, as shown in FIG. 1, a spectrum, suitably corrected from memory device 71, is recorded in memory A (function switch poles 66, 67 in rightward closing positions and switch pole 84 moved into engagement with contact 60A). With pole 84 released, the laser unit 44 is then set in the dotted view position of FIG. 2 and the sample is then flash-photolyzed (laser unit 44 optically coupled to light guides 36, 37). The optically corrected new spectrum is then recorded in memory B (function switch poles 66, 67 in rightward closing positions and switch pole 85 moved into engagement with contact 61A). With pole 85 released, the difference between the spectra in memories A and B can then be read out on recorder 48 by moving switch pole 50 into engagement with contact 53, with wavelength drive 46 in operation.

The optically corrected base line M minus R spectrum (no photolysis) or the optically corrected photolysis M minus R spectrum may be applied directly to the Y input terminal of the recorder by moving switch pole 50 into enggement with contact 52, with function switch poles 66, 67 respectively engaging contacts 76 and 74.

As above stated, the spectral effect of flash photolysis may be read out on the recorder 48 by subtracting the stored memory B spectum from the stored memory A spectrum. If, however, one wishes to record another difference spectrum at a later time, the memory A may be reset and filled with the new spectrum, the difference between the two stored spectra again being obtained as an input to the X-Y recorder. Thus, the spectrophotometer of the present invention provides, among others, the following important features: (1) a secure baseline can be obtained from a single sample; (2) flash activation of a portion of the sample is possible; (3) subtraction of spectra corresponding to flash activation or the progression of the kinetics in the sample is also possible.

FIG. 5 affords another example of the operation of the spectrophotometer. The configuration of the sample is indicated at the right. The baseline $a$ is taken with cytochrome $a_3$.CO present in the tube 23. (Note that the dotted vertical partition 91 in the tube merely indicates diagrammatically the separation afforded by the separate light guide coupling to the reference and measure portions of the tube). Trace $a$ represets the reading-in of the baseline to the computer memory A. The 585 nm liquid dye laser is light guide-coupled to the M side of the tube, and the flash liberates cytochrome $a_3$ from CO to give free ferrous $a_3$ and CO. No recombination occurs at $-130°$ C. The scanning spectrophotometer then records the difference of absorption between the $a_3$.CO compound and the ferrous cytochrome oxidase (Trace $b$). A second flash delivered to the R side of the sample now causes nearly equal absorbancy changes to occur in the two sections of the sample, giving Trace $c$. Since, however, a slight recombination of CO has occurred in the M sample portion due to its longer lifetime, a small peak 92 at about 590 nm appears in Trace c.

It will be seen that the arrangement disclosed in FIG. 4 provides a wide rang of flexibility in the comparison of M minus R difference spectra either as between photolyzed and non-photolyzed portions of a sample, as between portions photolyzed at different times, or as between the time-dependent differences of spectra of sequentially photolyzed portions.

It is to be noted that for data handling the is considerable convenience in employing the memory devices A and B; however, the main concept or principle of the present invention relies on generating an absorbancy difference in a homogeneous sample by flash activation of a portion of it.

The LDL 585 nm laser unit 44 is mounted on the guiding support 45 to allow it to be set selectively for adjustment for the exposure to the respective R and M light guide assemblies. This offers considerable convenience in alternately flash-illuminating two spaced parts of the sample tube if so desired. Basically, it is necessary to create the required asymmetry in the sample merely by flash-illuminating one part of the sample. Flash-illuminating first one part and then the other part should cause the asymmetry to decrease to zero, and the tube should be uniform in optically corrected properties again (some asymmetry may be intrinsic in the optical system). However, the main advantage of being able to flash first one portion and then the other is that the difference spectra between the two parts now become a time-series spectrum, in which one portion has been able to react for a known total time, while the second portion has reacted only for a known lesser time. Thus the happenings in the interval between the flashes are pictorially represented by the difference spectrum of the tube, and said difference spectrum is useful in understanding and evaluating the reaction kinetics.

While certain specific embodiment of methods and apparatus for analyzing oxidation-inhibited samples exposed to oxidizing agents and flash-photolyzed have been disclosed in the foregoing description, it will be understood that various modifications within the spirit of the invention may occur to those skilled in the art. Therefore it is intended that no limitations be placed on the invention except as defined by the scope of the appended claims.

What is claimed is:
1. A method of mesuring the kinetic reactions in a photo-reactive sample comprising establishing a condition wherein mixing of two portions of the sample enclosed in a common sample container is inhibited, exposing one portion to a photolyzing flash, determining the spectral absorbance of said two portions, and comparing the spectral absorbance of said one portion with that of the other portion.

2. The method of claim 1, and wherein the samle comprises CO-inhibited cytochrome oxidase containing an oxidizing reagent.

3. The method of claim 1, and wherein the comparison is made by obtaining a first spectral readout of the difference between the optical absorbances of the two portions before the photolysis, obtaining a second spectral readout of the difference between the optical absorbances of the two portions after the photolysis, and subtracting one spectral readout from the other spectral readout to thereby obtain a third difference spectrum.

4. The method of claim 1, and wherein said other portion of the sample is also exposed to a photolyzing flash, but at a time different from the time of flash photolysis of said one portion.

5. The method of claim 1, and wherein the mixing of the two portions is inhibited by holding the sample at a sufficiently low temperature to maintain it substantially in a solid condition.

6. An apparatus for measuring the kinetic reactions of a sample, comprising a source of variable wavelength scanning radiation providing two alternating time-shared monochromatic scanning beams, photosensitive means, a transparent sample container, optical guide means defining two respective optical paths traversing spaced portions of said container and respectively receiving said time-shared scanning beams and directing them through said space portions, said optical guide means having means to direct the emergent scanning beams to said photosensitive means, means to derive an absorbance difference spectrum for the two spaced portions from the output of said photosensitive means, and means to flash-photolyze at least one of said spaced portions.

7. The measuring apparatus of claim 6, and means to selectively flash-photolyze the two spaced sample container portions.

8. The measuring apparatus of claim 6, and wherein said source comprises a lamp, scanning monochromtor means receiving light from said lamp, and beam-splitting means receiving monochromatic light from said monochromator means and generating said alternating time-shared scanning beams.

9. The measuring apparatus of claim 6, and wherein said optical path-defining means comprises light guide means optically traversing said two spaced portions and respectively receiving said scanning beams and guiding the scanning beams through said two spaced portions, said light guide means having end light output means exposed to said photosensitive means.

10. The measuring apparatus of claim 9, and wherein the means to flash-photolyze the sample container portion comprises a light flash source and auxiliary light guide means between said light flash source and said sample container and having an output end exposed to the sample container at a point adjacent to but angualrly spaced from the traversal path of the associated scanning beam.

11. The measuring apparatus of claim 10, and wherein said auxiliary light guide means is in a plane perpendicular to the plane of the scanning beam traversal paths, said paths being parallel to each other.

12. The measuring apparatus of claim 10, and wherein an auxiliary light guide means is provided for each of said sample container spaced portions and the flash-photolyzing means is provided with means to selectively illuminate the auxiliary light guide means.

13. The measuring apparatus of claim 12, and wherein the scanning beam traversal paths are parallel to each other and wherein both of the auxiliary light guide means are in a common plane substantially perpendicular to that of the scanning beam traversal paths.

14. The measuring apparatus of claim 12, and means adjustably supporting the flash-photolyzing means so that it can selectively illuminate the two auxiliary light guide means.

15. The measuring apparatus of claim 6, and means to compare the absorbance difference spectra before and after flash photolysis.

16. The measuring apparatus of claim 15, and wherein the comparison means comprises means to subtract the absorbance difference spectrum after said photolysis from the absorbance difference spectrum before said photolysis and to derive therefrom a third difference spectrum.

17. The measuring apparatus of claim 6, and means to hold the sample container at a sufficiently low temperture to inhibit mixing of the sample contained in said two space portions.

* * * * *

UNITED STATES PATENT OFFICE
CERTIFICATE OF CORRECTION

Patent No. 4,023,905     Dated May 17, 1977

Inventor(s) Britton Chance

It is certified that error appears in the above-identified patent and that said Letters Patent are hereby corrected as shown below:

Column 1, line 33, "oxidizig" should read -- oxidizing --.

Column 3, line 68, "tranparent" should read -- transparent --.

Column 4, line 56, "spectrohotme-" should read -- spectrophotome- --.

Column 5, line 31, "assosicated should read -- associated --.

Column 6, line 3, "subesequent" should read -- subsequent --.

Column 6, line 31, "enggment" should read -- engagement --.

Column 6, line 36, "specturm" should read -- spectrum --.

Column 7, line 4, "rang" should read -- range --.

Column 7, line 10, "the" should read -- there --.

Column 7, line 49, "mesuring" should read -- measuring --.

Column 7, line 57, "samle" should read -- sample --.

Column 8, line 17, "space" should read -- spaced --.

Column 8, line 46, "gualrly" should read -- gularly --.

Column 10, line 6, "space" should read -- spaced --.

Signed and Sealed this nineteenth Day of July 1977

[SEAL]

Attest:

RUTH C. MASON
*Attesting Officer*

C. MARSHALL DANN
*Commissioner of Patents and Trademarks*